US006461323B2

(12) United States Patent
Fowler et al.

(10) Patent No.: US 6,461,323 B2
(45) Date of Patent: Oct. 8, 2002

(54) SURGICAL SYSTEM PUMP WITH FLOW SENSOR AND METHOD THEREFOR

(76) Inventors: Reginald H. Fowler, 302 S. Fuller, Meridian, TX (US) 76665; Garrett L. Barker, P.O. Box 594, Meridian, TX (US) 76665; C. Kenneth French, HC 65 Box 10D, Meridian, TX (US) 76637

( * ) Notice: Subject to any disclaimer, the term of this patent is extended or adjusted under 35 U.S.C. 154(b) by 8 days.

(21) Appl. No.: 09/805,349

(22) Filed: Mar. 13, 2001

(65) Prior Publication Data

US 2001/0039398 A1 Nov. 8, 2001

Related U.S. Application Data

(63) Continuation-in-part of application No. 09/564,014, filed on May 3, 2000.

(51) Int. Cl.⁷ .............................................. A61M 31/00
(52) U.S. Cl. ........................... 604/67; 604/31; 604/151; 417/43; 417/63
(58) Field of Search ................................ 604/151, 131, 604/66, 67, 27, 30–34, 118, 140; 417/43, 63, 423.1

(56) References Cited

U.S. PATENT DOCUMENTS

| | | | | |
|---|---|---|---|---|
| 4,940,457 A | * | 7/1990 | Olson | 604/122 |
| 5,391,145 A | | 2/1995 | Dorsey, III | 604/33 |
| 5,484,402 A | | 1/1996 | Saravia et al. | 604/35 |
| 5,609,576 A | * | 3/1997 | Voss et al. | 128/925 |
| 5,718,668 A | | 2/1998 | Arnett et al. | 601/155 |
| 5,807,313 A | | 9/1998 | Delk et al. | 604/35 |
| 5,882,339 A | * | 3/1999 | Beiser et al. | 604/153 |
| 6,106,494 A | * | 8/2000 | Saravia et al. | 604/151 |
| 6,148,857 A | * | 11/2000 | West et al. | 137/596.2 |
| 6,176,847 B1 | * | 1/2001 | Humphreys et al. | 604/246 |

OTHER PUBLICATIONS

Chiron Surgiflex Wave XP suction irrigation probe with battery powered pump. Catalog sheet from Chiron web site, circoncorp.com, Feb. 1, 2001, 6 web pages plus two pages digital photographs.

* cited by examiner

Primary Examiner—Brian L. Casler
Assistant Examiner—Mark Han
(74) Attorney, Agent, or Firm—Robert C. Kain, Jr.; Fleit Kain

(57) ABSTRACT

The automatically controlled pump supplies pressurized irrigation fluid to a surgical site. The pump system includes a motor in a housing and a pump in a housing defining input and output ports. The pump has a rotatable impeller. The motor is powered by one or more batteries. An ON/OFF motor switch is controlled by fluid flow above a nominal flow by a sensor typically mounted downstream of the pump. The system operates in conjunction with a downstream manual control valve. Flow above a system minimal flow is detected by a negative buoyancy poppet having a "leaky" valve seat. When the poppet moves into a flow chamber, the switched motor is ON. Various position sensors may be used, i.e., an optical sensor. The method automatically controls a pump by monitoring fluid flow above a system minimal flow and turning ON/OFF the motor based upon flow above the minimum.

14 Claims, 9 Drawing Sheets

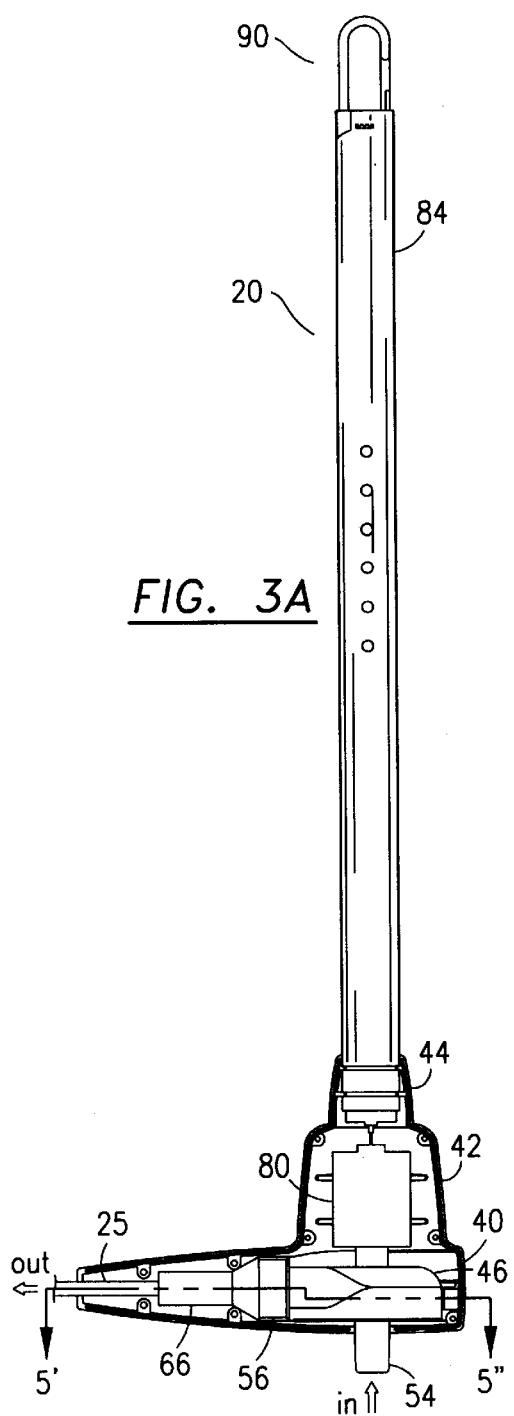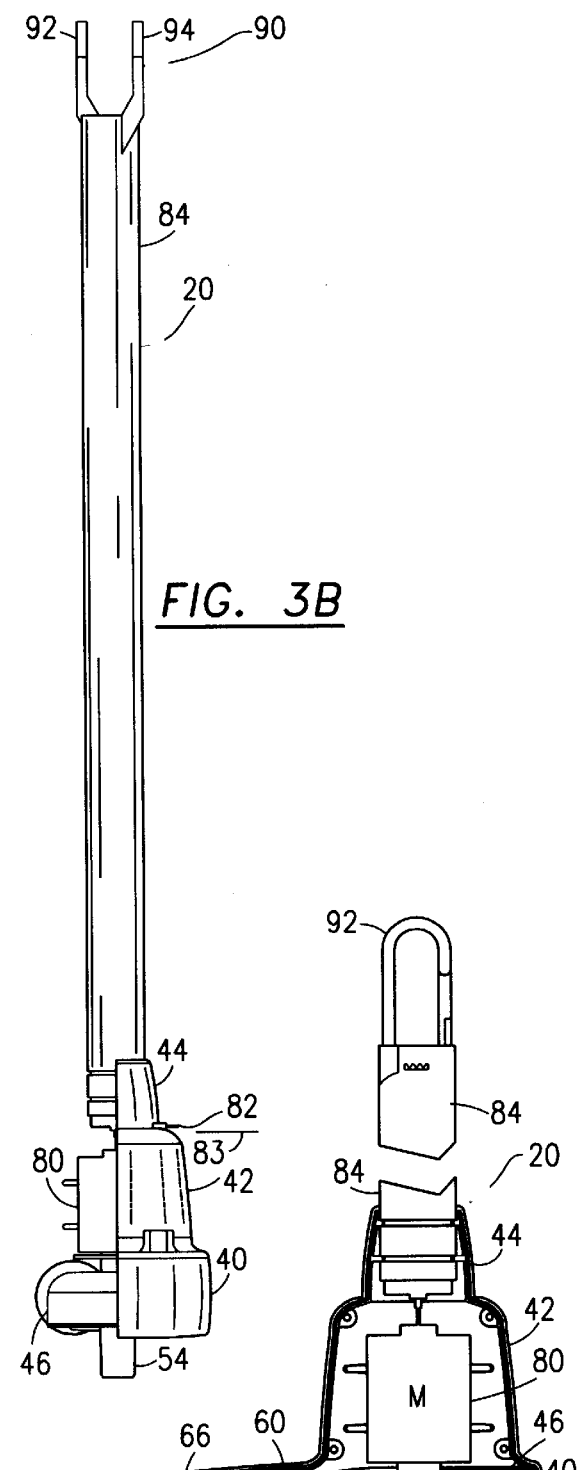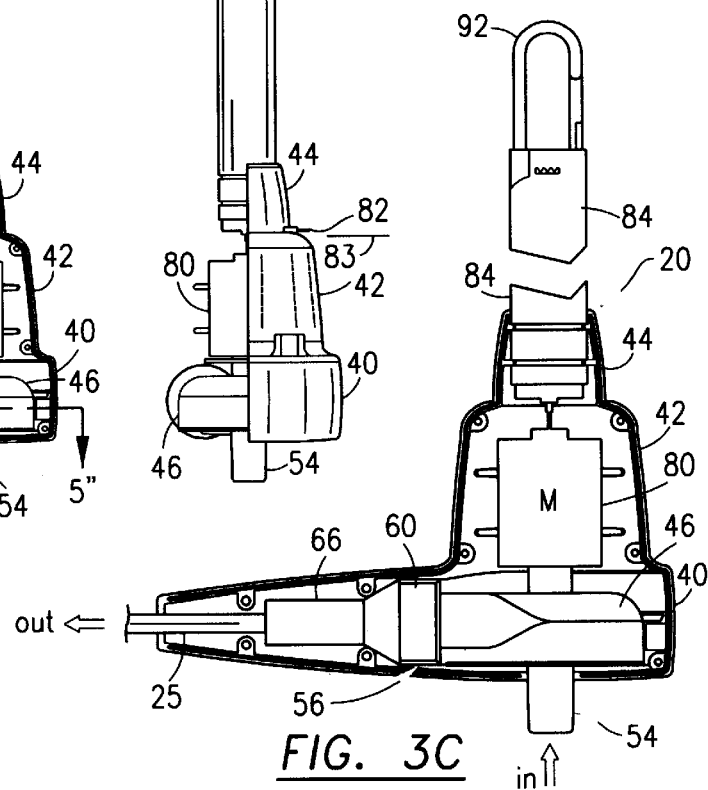

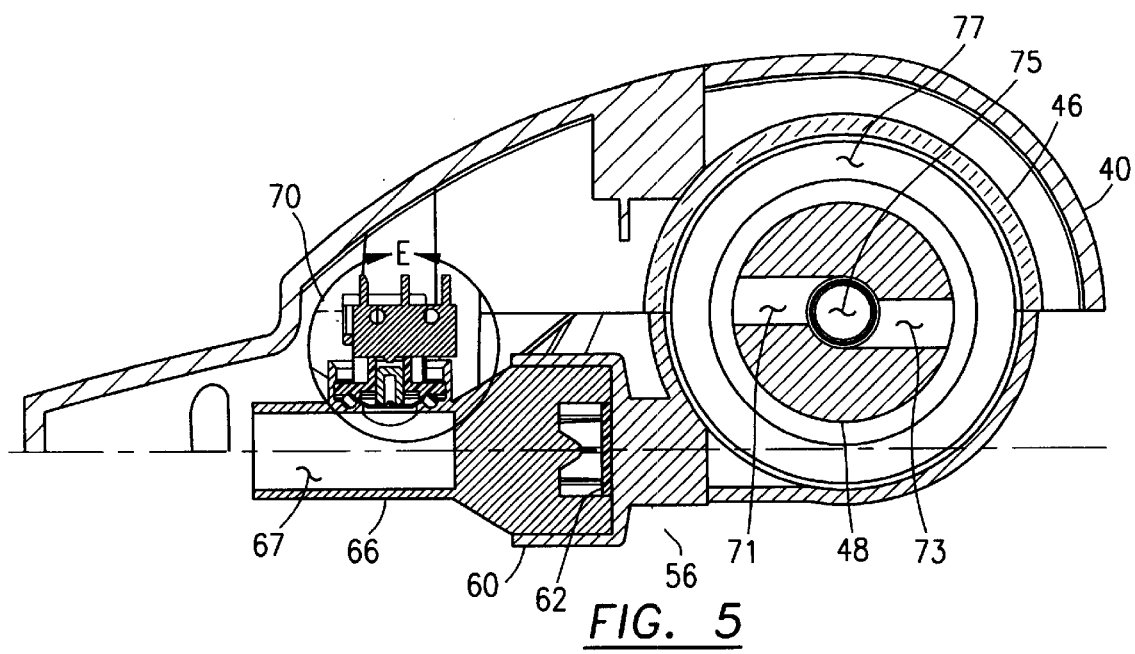
FIG. 5
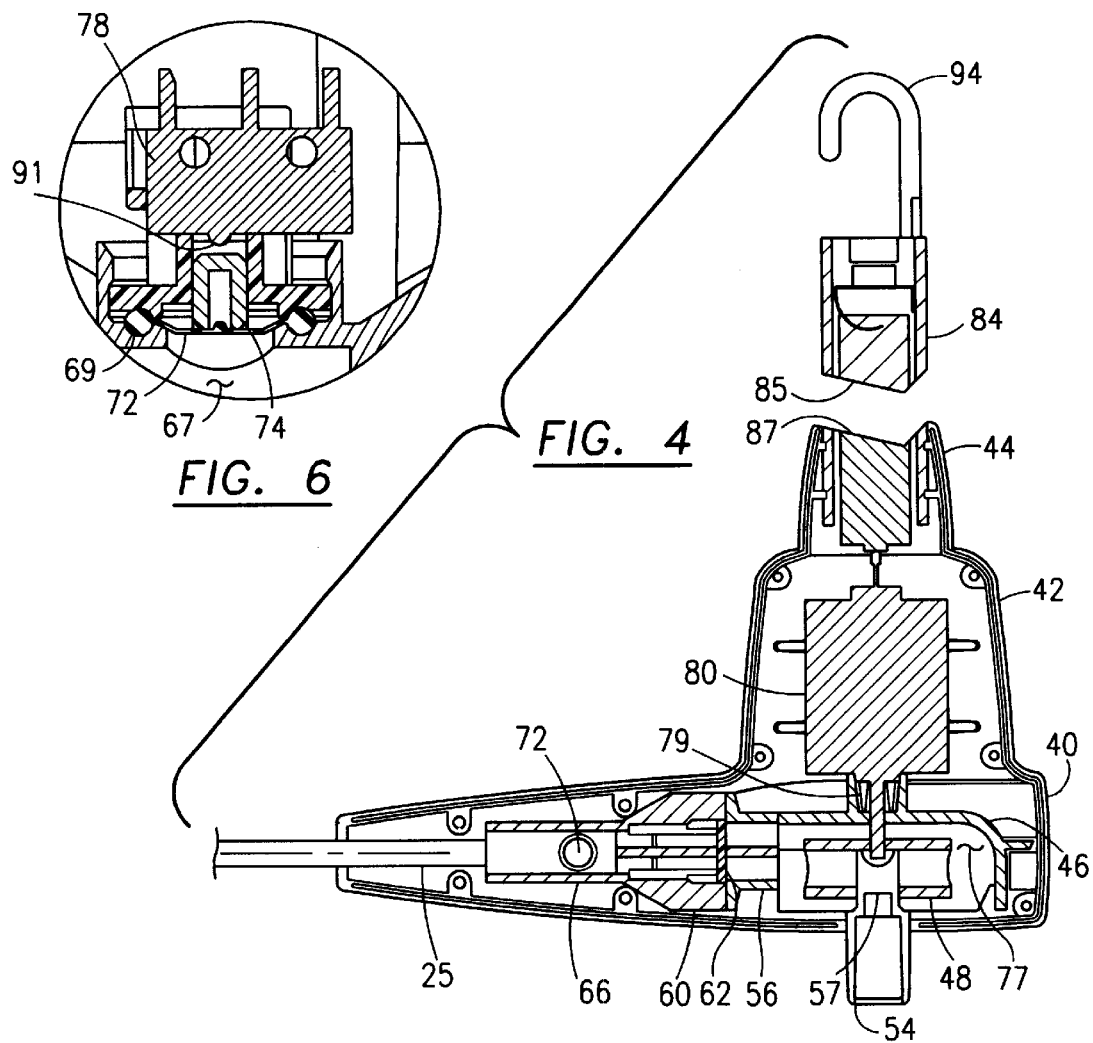
FIG. 6
FIG. 4

SURGICAL SYSTEM PUMP WITH FLOW SENSOR AND METHOD THEREFOR

This is a continuation-in-part of U.S. patent application Ser. No. 09/564,014, filed May 3, 2000, now pending.

The present invention relates to an automatic pump system, typically used to supply pressurized irrigation fluid to a surgical site, and a method therefor.

BACKGROUND OF THE INVENTION

In many instances, a physician and other health professional (sometimes referred to herein as an "operator") utilizes irrigation fluid to cleanse and wash a wound at a surgical site. This irrigation fluid (sometimes generally referred to herein as "fluid") is specially prepared for this medical procedure. In many instances, the fluid is retained at a fluid source which, in most situations, is a sterile bag containing irrigation fluid. Sterilized water is typically used in such medical procedures.

The physician or operator controls the flow of irrigation fluid by a simple valve control or valve unit at or near the surgical site. In some instances, this valve unit includes a second valve which controls suction such that the physician or operator can remove irrigation fluid, debris and other bodily fluids from the surgical site by activating the second valve in the valving unit and drawing the spent irrigation fluid from the surgical site with a vacuum or suction line.

U.S. Pat. No. 5,807,313 to Delk et al. discloses a battery powered surgical irrigator system. In this prior art system, an electrical switch is mounted immediately adjacent the valve unit which controls the flow of irrigation fluid. The valve unit includes an irrigation fluid valve and a suction valve. In order to turn ON and OFF the pump supplying pressurized irrigation fluid, the operator depresses an electrical control switch mounted on the valving unit. The pump is located beneath the bag holding the supply of irrigation fluid.

U.S. Pat. No. 5,484,402 to Saravia et al. discloses a surgical suction irrigator. In this system, the irrigation and suction valve control also enclose and include an electrical switch. The pump which supplies pressurized fluid to the valve unit, is mounted beneath the bag of irrigation fluid.

U.S. Pat. No. 5,718,668 to Arnett et al. discloses an irrigation hand piece with a built in pulsating pump. This system utilizes a hand piece which includes a pump, a battery power supply for the pulsating pump motor and an electrical switch all mounted in the suction and irrigation valve unit.

Some battery powered irrigation pump systems, used in surgical suites, turn ON and OFF the pump based upon a floating poppet. The floating poppet is disposed at the output of the pump. The floating poppet drops downward in its vertically oriented chamber and a Hall effect sensor determines this shift in the poppet's position and turns ON the pump. When the poppet rises due to the closure of a valve control downstream of the battery operated pump, the Hall effect sensor changes state and turns OFF the pump.

OBJECTS OF THE INVENTION

It is an object of the present invention to provide an automatic pump system which eliminates the need for a manual or operator actuated switch to turn ON and OFF the pump supplying a pressurized supply of surgical fluid to the surgical site.

It is another object of the present invention to provide an automatically controlled pump wherein the pump control monitors fluid flow at the input or the output of the pump thereby ensuring a pressurized supply of surgical fluid to the surgical field via a remotely disposed valving unit.

It is an additional object of the present invention to provide a disposable automatic pump system for a surgical suite.

It is another object of the present invention to provide a method for automatically controlling an irrigation supply pump wherein fluid flow is monitored at the pump output and, based upon fluid flow above a system minimal flow, a negative buoyancy poppet leaves a "leaky" valve seat, moves into a large flow segment of a valve chamber pressure and turns ON the motor and the pump due to a changed state of a position sensor (preferably, an optical sensor) and the application of battery power to the motor driving the pump.

SUMMARY OF THE INVENTION

The automatically controlled pump supplies pressurized irrigation fluid via an output line to a surgical site. The pump is coupled to a fluid source via an input line. The pump system includes a motor, a motor housing, a pump disposed within a pump housing and fluid input and fluid output ports defined by the pump housing. The pump has a rotatably disposed impeller coupled to the motor. The input and output lines are respectively coupled to the fluid input and output ports. The motor is powered by at least one battery and preferably a plurality of batteries. A switch turns ON and OFF the motor and is controlled by fluid flow above a system minimal flow. The system operates in conjunction with a manual flow control valve (a fluid control valving system) actuated by an operator downstream of the battery powered pump. The fluid flow sensor is typically mounted downstream of the pump output. Fluid flow is monitored at the pump output and, based upon fluid flow above a system minimal flow, a negative buoyancy poppet leaves a "leaky" valve seat, moves into a large flow segment of a valve chamber pressure and turns ON the motor and the pump due to a changed state of a position sensor (preferably, an optical sensor) and the application of battery power to the motor driving the pump. The method of automatically controlling a pump includes providing a battery powered motor mechanically coupled to the pump, the step of monitoring fluid flow above a system minimal flow and turning ON and OFF the motor based upon fluid flow above the system minimum.

BRIEF DESCRIPTION OF THE DRAWINGS

Further objects and advantages of the present invention can be found in the detailed description of the preferred embodiments when taken in conjunction with the accompanying drawings in which:

FIGS. 3A and 3B diagrammatically illustrate partial, cross-sectional views of the automatic pump system;

FIG. 3C diagrammatically illustrates a detailed, cross-sectional view of the pump system;

FIG. 4 diagrammatically illustrates a detailed, cross-sectional view of the pump system showing the lower portion of the battery housing, the motor, the pump impeller, the pump's input port and the pump's output port;

FIG. 5 diagrammatically illustrates a partial, cross-sectional view of the pump system impeller, output port and fluid pressure sensitive switch generally from the perspective of section line 5'–5" in FIG. 3A;

FIG. 6 diagrammatically illustrates the preferred embodiment of the pressure sensitive switch from detail area E in FIG. 5;

DETAILED DESCRIPTION OF THE PREFERRED EMBODIMENTS

The present invention relates to an automatically controlled pump or pump system for supplying pressurized fluid to a surgical site and a method therefor and an irrigation surgical kit.

Figure 1A:
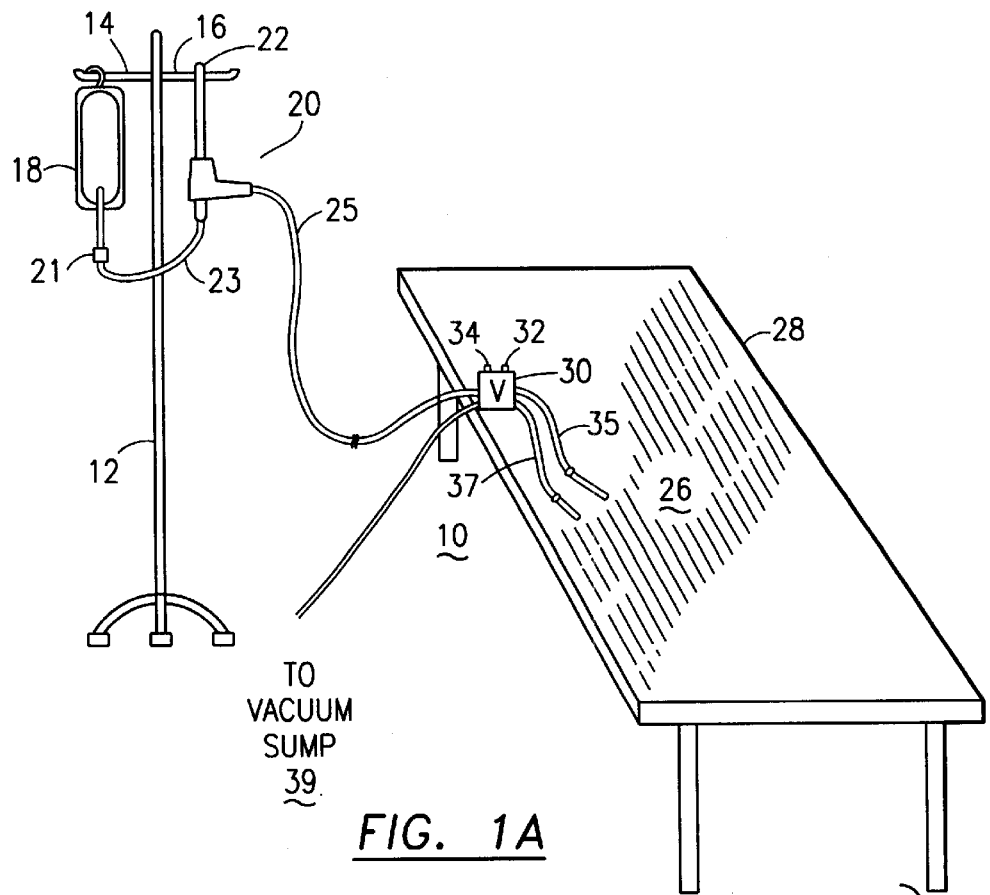
FIG. 1A diagrammatically illustrates certain aspects of a surgical suite including the source of surgical fluid (irrigation fluid), an automatic pump system provided in accordance with the principles of the present invention, input and output lines, and an operator controlled irrigation and suction unit (collectively, an irrigation surgical kit except for the source of fluid)

FIG. 1A diagrammatically illustrates a surgical suite, or the relevant portions thereof, in suite 10. Suite 10 includes a stand 12 which has hanger bars 14, 16. A source of irrigation fluid is found in bag 18 hung on hanger bar 14. Automatic pump 20 is hung via terminal end 22 on hanger bar 16. In the preferred embodiment, automatic pump system 20 is disposable. Pump system 20 is supplied with fluid via input line 23. Pump system 20 supplies pressurized fluid via output line 25 to the surgical site generally located in area 26 on table 28. An operator controls the flow of fluid, typically irrigation fluid, via valve system 30. In many situations, valve system 30 includes an irrigation line control valve 32 and a suction line control valve 34 and respective suction and irrigation lines 35, 37 extending from valve unit 30 to surgical site 26. Suction line 37, after passing through valve unit 30, is coupled to a vacuum source and sump 39.

There are many different types of valve control units that may be used in connection with the automatic pump system and kit in accordance with the principles of the present invention. For example, U.S. Pat. No. 5,522,796 to Dorsey; U.S. Pat. No. 5,188,591 to Dorsey; U.S. Pat. No. 5,391,145 to Dorsey; U.S. Pat. No. 5,391,145 to Dorsey and U.S. Pat. No. 5,573,504 to Dorsey disclose operator controlled valving systems. Valve system or unit 30 is sold as part of an irrigation surgical kit which additionally includes output line 25 (typically about 12 feet in length), automatic pump 20, input line 23 (typically 12 inches in length) and spike 21. Pump 20 is preferably disposable. The batteries (size AA) are removed by "cracking open" the battery housing. Although the present invention is primarily directed toward pump system 20, in some instances, automatic pump system 20 is incorporated into a surgical kit which includes the aforementioned items. Various valve systems 30 may be utilized in connection with automatically controlled pump 20.

Figure 1C:
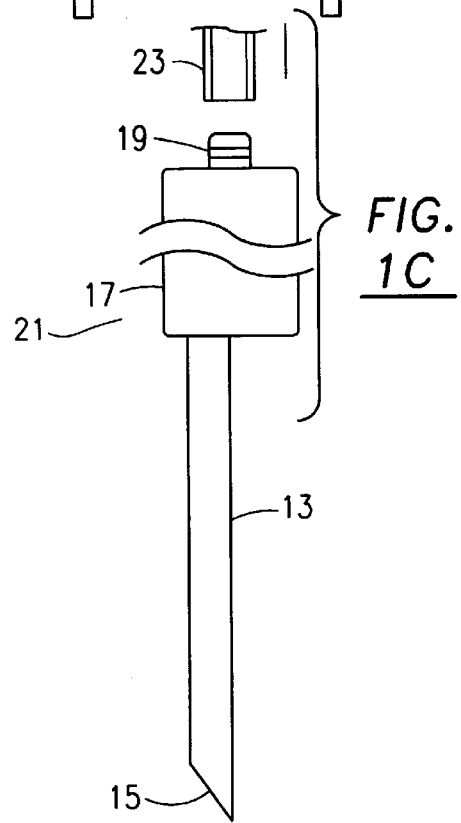
FIG. 1C diagrammatically illustrates the spike utilized to provide fluid access to the source of surgical fluid (the bag)
Figure 1B:
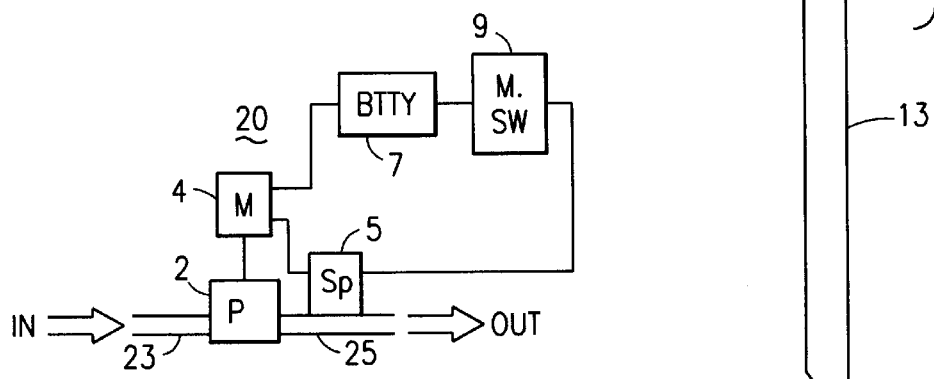
FIG. 1B diagrammatically illustrates a block diagram showing fluid control and electrical components of the automatic pump system in accordance with the principles of the present invention.

FIG. 1B diagrammatically shows the fluid control and electrical system for the present invention. Pump P2 is mechanically driven by motor M4. Pump P is supplied with a source of fluid via input line 23. Pump P generates pressurized fluid (when motor M is turned ON) on output line 25. As used herein, the term "pressurized fluid" or the phrase "a pressurized supply of surgical fluid" refers to fluid under a pressure greater than the fluid pressure in input line 23. Typically the pressure in output line 25, when pump P is turned ON, is approximately 5 psi.

One of the key features of the present invention is the use of a fluid pressure sensitive switch Sp 5 which is mounted or disposed at or near the output port of pump P. Pump system 20 automatically detects when the pressure in output line 25 falls below a predetermined value (approximately 5 psi). Upon detecting that low pressure, switch Sp closes the electrical circuit between battery 7 and motor M. In addition, the operator is provided with a manual ON switch 9. In most instances, after pump 20 is mounted on hanger bar 16 or is otherwise placed in use, the operator closes manual switch 9 and the pump operates automatically. Sometimes, the fluid or hydraulic system must be primed or filled with fluid before the pump operates automatically. When pressure in output line 25 falls below a predetermined value (or a range of values), switch Sp closes thereby supplying electrical power to motor M which drives pump P which further supplies pressurized fluid to output line 25. When the correct pressure is achieved in line 25, the switch opens, power is removed from the motor and the pump stops.

Referring to FIG. 1A, the basic diagram of a surgical suite, pressurized fluid (typically irrigation fluid) is supplied via output line 25 to the operator controlled valving unit 30. Valving unit 30 is typically disposed at a remote location away from stand 12 that holds fluid supply 18 and pump system 20. By providing an automatic ON and OFF control and generally uniform pressure in output line 25, the physician or operator, by closing irrigation valve (either valve 32 or valve 34) in valving unit 30, can deliver a controlled constant flow or a variable flow (dependent upon the position of valve 32) of irrigation fluid to surgical site 26.

The present system avoids the use of an additional electrical line mechanically coupled and extending along the length of fluid output line 25 to an electrical motor in pump system 20. See U.S. Pat. No. 5,807,313. Further, the present invention avoids the necessity of an operator controlled ON/OFF switch in addition to irrigation and suction valve controls 32, 34 at valving unit 30. The reduction of operator controls enhances the operator's ability to more efficiently clean and treat the wound or other item at surgical site 26.

FIG. 1C diagrammatically shows spike 21 which includes a rigid tube 13, a sharp end 15, a hand piece 17, and a hose coupling unit 19.

Figure 2:
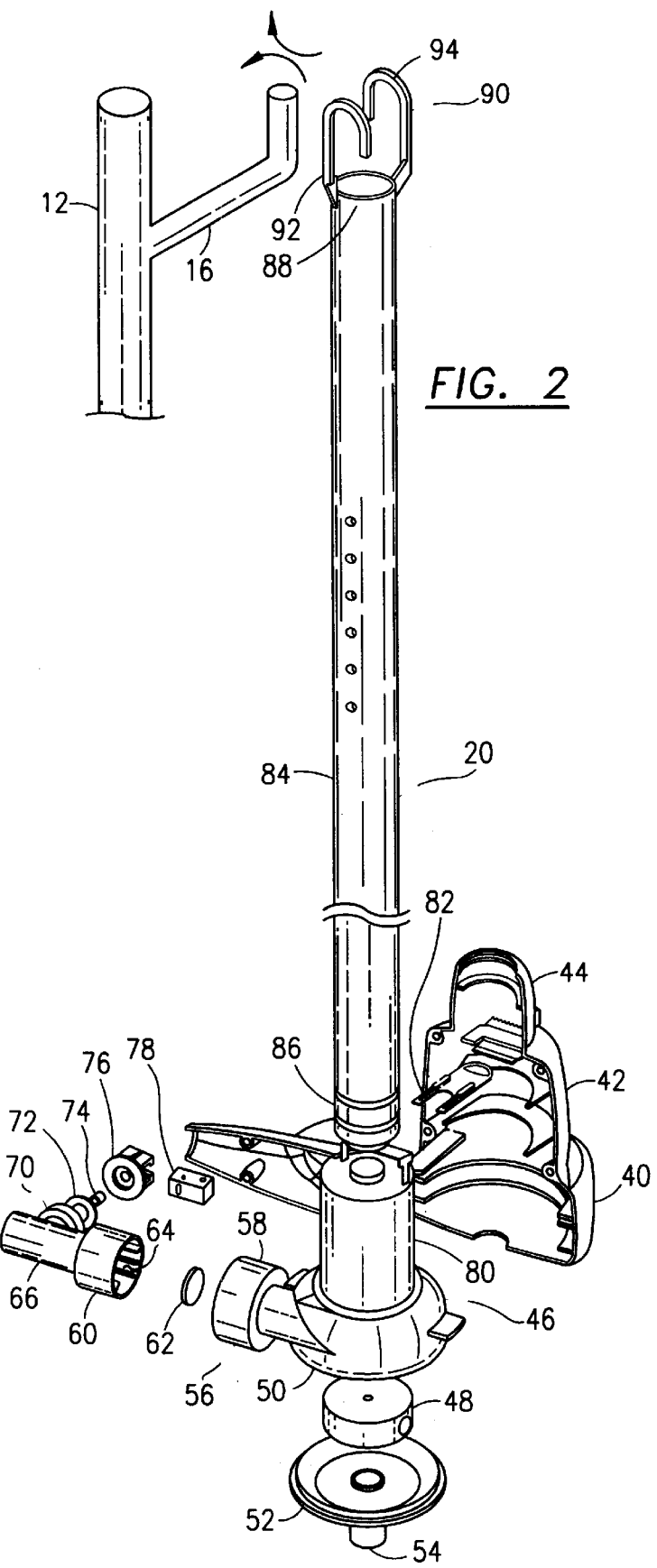
FIG. 2 diagrammatically illustrates a partial, exploded, perspective view of the automatic pump system and the hanger mechanism to mount the pump system on the medical stand.

FIG. 2 diagrammatically shows automatic pump system 20 as a partial, exploded view. Pump system 20 includes exterior pump housing 40, motor housing 42 and collar 44. Exterior pump housing 40 contains interior pump housing 46. A chamber inside interior pump housing 46 is established to rotatably contain pump impeller 48. Interior pump housing 46 includes upper housing 50 and a lower housing 52. In one embodiment, lower housing 52 is threadibly attached (with a fluid and pressure seal) to upper housing 50. Impeller 48 rotates in a chamber (identified later) established between upper and lower housings 50, 52. Alternatively, the lower housing may be solvent bonded or snap fit onto the upper housing.

Pump housing 46 defines a fluid input port 54 and a fluid output port 56. Fluid output port 56 includes proximal body 58 and distal body 60. A check valve having a check valve disc 62 is mounted in interior space 64 defined by proximal and distal output port bodies 58, 60. Pump output port 56 also includes nozzle body 66. A fluid pressure sensitive switch 70 is mounted thereon. Fluid pressure sensitive switch 70 is mounted downstream of the check valve and particularly check valve disc 62. However, pressure sensitive switch 70 is mounted at or near the pump's output port 56.

Pressure sensitive switch 70 includes a diaphragm 72 which limits fluid flow from the interior of nozzle 66 to the electrical components within switch 70 and the mechanical actuator member 74. Actuator member 74 moves within switch body 76. Switch body 76 also includes a fluid sealing system to limit fluid flow from the interior of nozzle body 66. Pressure sensitive switch 70 also includes a small electrical switch 78 which is sometimes referred to as a "micro switch." Micro switch 78 is electrically connected to motor 80.

Motor 80 is mounted within motor housing 42. The drive shaft of motor 80 is mechanically coupled to pump impeller 48. A manual ON/OFF switch 82 enables the operator to pull slide switch 82 outward or outbound thereby closing the electrical contact between the batteries in battery housing 84 and the balance of the electrical circuit which includes the motor. Battery housing 84 has a proximal end 86 attached to collar 44 and to the upper portion of motor housing 42. Housing 84 also has a distal, terminal end 88. A hanger system 90 is defined at the terminal end 88 of battery housing 84. In the illustrated embodiment, two, inverted J-shaped clip bodies 92, 94 are utilized to provide a hanging system to hang pump system 20 on hanger bar 16 of medical stand 12. See FIG. 1A. One of the J-shaped clips opens in a direction opposite the other J-shaped clip.

Similar numerals designate similar items throughout the drawings.

FIGS. 3A and 3B diagrammatically illustrate partial, cross-sectional front views and side views of pump system 20. As shown in FIG. 3A, pump input port 54 receives fluid from the fluid supply. Nozzle housing 66 which is part of output port 56 is fluidly coupled to output hose 25. Hose 25 is adapted to fit snugly onto nozzle housing 66 and the hose carries the pressurized fluid to surgical site 26 (see FIG. 1A).

FIG. 3B diagrammatically shows pump system 20 and hanger clips 92, 94 being laterally spaced apart. FIG. 3B also shows operator actuable slide switch 82 which is moved in the direction of arrow 83 in order to turn the entire pump system ON. As described earlier, in the best mode of the present invention, pump system 20 is disposable. Once switch 82 is closed (by pulling out the slide), the pump must be used and then discarded.

Some important features of the present invention include pump system 20 capable of being hung on hanger arm 16 of medical stand 12; and the physical relationship between battery housing 84, motor 80 and pump housing 46 (which defines one of the major elements of the pump) by vertically aligning these three elements. With this hanger feature, automated pump 20 can hang at any convenient location near the source of fluid which is fluidly attached to pump system 20 at input port 54. Another feature is output port 56 (including nozzle 66) being disposed laterally with respect pump housing 46 and disposed above input port 54. One of the primary features of the invention is the use of a pressure sensitive switch near output port 56.

FIG. 3C shows a detailed, partial cross-sectional view of automated pump 20. Motor 80 is mounted securely within motor housing 54. Battery housing 84 is attached at the upper portion of motor housing 42 via collar 44. Pump housing 46 is mounted securely within external pump housing 40.

FIG. 4 diagrammatically illustrates a partial, cross-sectional view of the internal components of automated pump system 20. Battery housing 84 contains a plurality of batteries, two of which are batteries 85, 87. These batteries are currently AA sized. Impeller 48 is mechanically connected to motor 80 via a shaft with appropriate seals 79. Impeller 48 rotates within chamber 77. The rotation of impeller 48 draws fluid into input port 54. In the present embodiment, the pump is a centrifugal pump and impeller 48 rotates and draws fluid from input port 54 disposed beneath impeller 48. As impeller 48 rotates, the pressure in the fluid increases and the fluid is ejected through the check valve system which includes check valve disc 62 at output port 56. Fluid flow continues through check valve 62 and nozzle body 66. Pressure sensor diaphragm 72 senses the fluid pressure at a point immediately downstream check valve 62. Pressurized fluid is ejected through hose nozzle 66 to hose 25. To increase fluid flow, inboard end 57 of input port 54 is centrally located, on the axial centerline, and is positioned inboard of impeller 48. This inboard positioning increased flow about 0.25 l/min.

FIG. 5 shows a partial, cross-sectional, detailed view of the pump mechanism and its output port. Impeller 48 rotates and ejects fluid from internal passage 75 out through radial passages 71, 73. Fluid flow is ejected by impeller 48 into pump chamber 77. The resulting high pressure fluid exits pump output port 56 through check valve disc 62 and other common components of the check valve and through nozzle element 66. Fluid pressure sensitive switch 70 is immediately downstream of check valve 62 and either at or near pump output 56.

FIG. 6 shows a detailed view of fluid pressure sensitive switch 70 shown in detail area E in FIG. 5. Diaphragm 72 is sealed by seal 69 such that based upon fluid pressure in nozzle area 67, diaphragm 72 moves actuator pin or rod 74 towards or away from switch actuator 91. Switch actuator 91 operates to mechanically open or close the electrical switch in micro switch 78.

Although the present invention is shown utilizing various simple components such as a centrifugal pump and a micro switch activated by diaphragm, other pumps and switches can be utilized.

In operation, after the hydraulic system is connected and a fluid path is established from fluid source 18 through input line 23 to automatic pump 20, output line 25, manual valve control unit 30 (the system is "primed"), the operator pulls slide switch 82 (FIG. 2, FIG. 3B) and generally activates the automatic pump ON. Switch 78 is generally a normally closed switch. Since the pressure in output line 25 is less than the predetermined amount (herein approximately 5 psi), and since micro switch 78 is normally closed, the battery power is applied to motor M thereby turning ON the motor and driving impeller 48. Impeller 48 then pulls fluid into input port 54 and ejects fluid under pressure to output line 25. When the pressure in output line 25 exceeds a predetermined value established by diaphragm 72 and any biasing mechanism (e.g. spring or tension fit of the diaphragm), actuator pin 74 depresses actuator lever 91 and switch 78 opens the electrical circuit and turns the motor OFF. When the pressure falls below the predetermined value in output line 25, diaphragm 72 senses and reacts to the pressure and moves actuator 74 outboard away from mechanical actuator 91 and turns switch 78 to its normally closed ON position thereby reestablishing an electrical circuit between the batteries and motor 80. Preferably, diaphragm 72 is made of silicone. Various types of biasing mechanism such as springs or a tension established on diaphragm 72 may be utilized. Other types of pressure sensors may be utilized, for example, digital pressure sensors. These sensors may require digital circuitry.

Although the currently proposed system has the pressure sensitive switch near output port 56, the system will work if the pressure sensitive switch is fluidly coupled anywhere between the pump output and valving unit 30.

The automatic pump system described in connection with FIGS. 7 through 16 also supplies pressurized irrigation or surgical fluid via an output line to a surgical site. Unlike the pressure controlled system described above, the system described below in connection with FIGS. 7 through 16 utilizes a fluid flow control feedback. The fluid flow control utilizes a poppet as a position sensor. In the preferred embodiment, the poppet includes a negatively buoyant ball that rises perpendicularly with respect to a "leaky" or non-sealing valve seat. The flow sensor and irrigation fluid source is elevated above the valve control near the surgical site. See FIG. 1A.

Figure 7:
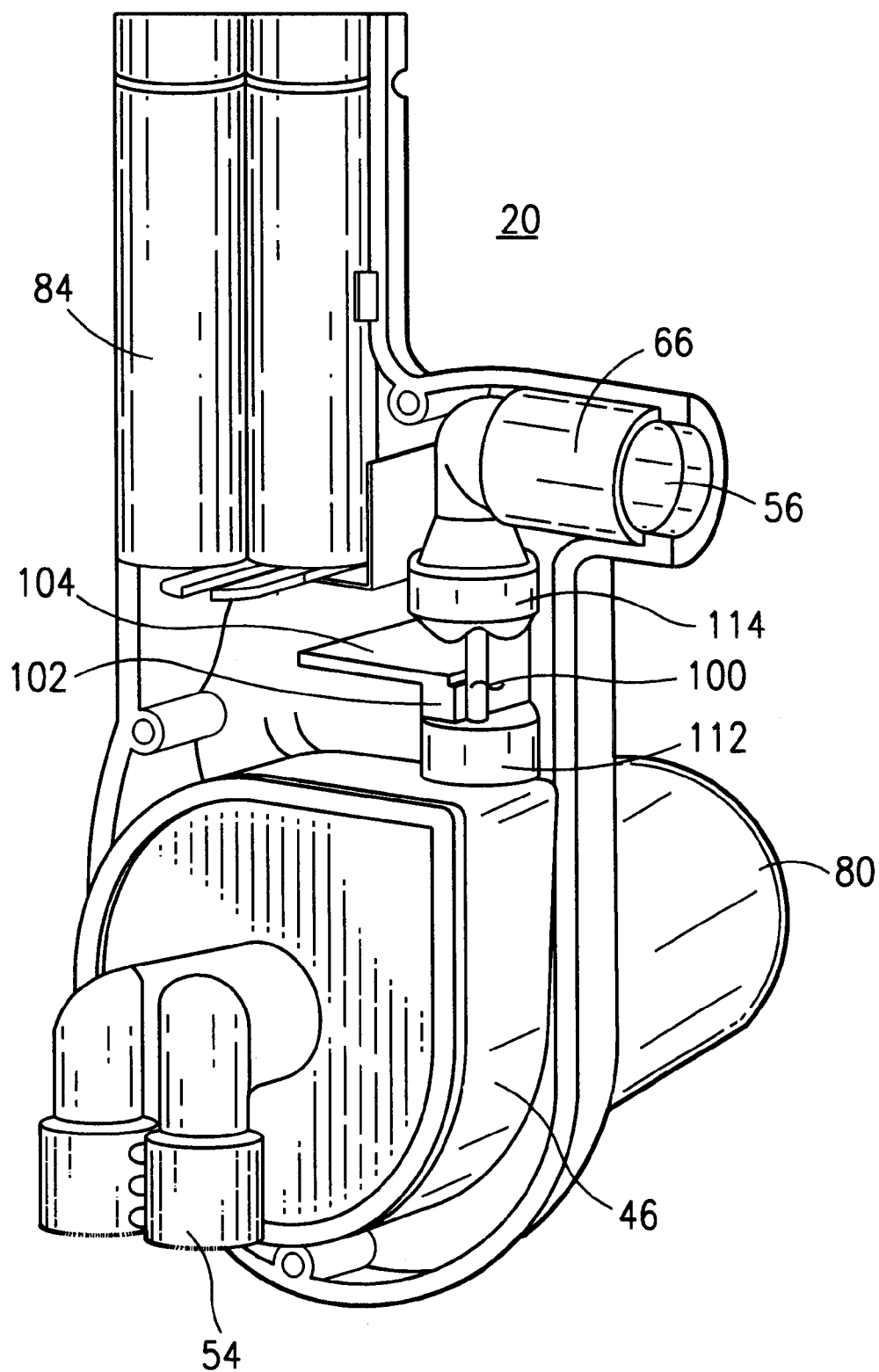
FIG. 7 diagrammatically illustrates a cut-away view of the pump system with an optical switch platform for monitoring fluid flow at the output of the pump impeller chamber.

FIG. 7 diagrammatically illustrates a cut-away view of the automatic pump system 20. Pump system 20 includes flow sensor 100 with a flow chamber 110 (see FIG. 8) located above the pump and inner pump housing 46. Flow sensor 100 could be moved below the pump such that flow sensor 100 is fluidly coupled to the pump input fluid port. Flow chamber 110 includes a small flow segment or chamber 112 and a large flow segment or chamber 114 adjacent thereto. Within flow chamber 110 is a poppet, preferably a poppet ball, 106 (see FIG. 8), capable of moving between small flow segment 112 and large flow segment 114. Adjacent the small flow segment 112 is an optical sensor 102 which senses the movement or presence of poppet 106 within flow chamber 110. Optical sensor 102 could also be adjacent large flow segment 114 (rather than as illustrated adjacent the small flow segment). Optical sensor 102 includes circuitry 104 electrically coupling optical sensor 102 to the electrical system for motor 80. In FIG. 7, the circuitry is represented by a circuit board 104 adjacent flow sensor 100. The circuitry may be located anywhere within the system. Optical sensor 102 includes, in a preferred embodiment, an infrared transmitter and receiver as an optical switch. Although the preferred embodiment includes an optical sensor, various other position sensors could be utilized such as EMF sensors, Hall effect sensors, RF sensors and magnetic sensors.

FIG. 7 also illustrates fluid input port 54 as a dual inlet. Input port 54 may also include a single inlet and is fluidly coupled to the pump input fluid port. Internally, the pump includes substantially the same components as the pump utilized with the automatic system described above in connection with FIGS. 1A through 6. The pump also functions in much the same manner. Fluid output port 56 is above flow sensor 100. The automatic pump system 20 illustrated in FIG. 7 also includes battery housing 84, which houses at least two batteries.

Figure 8:
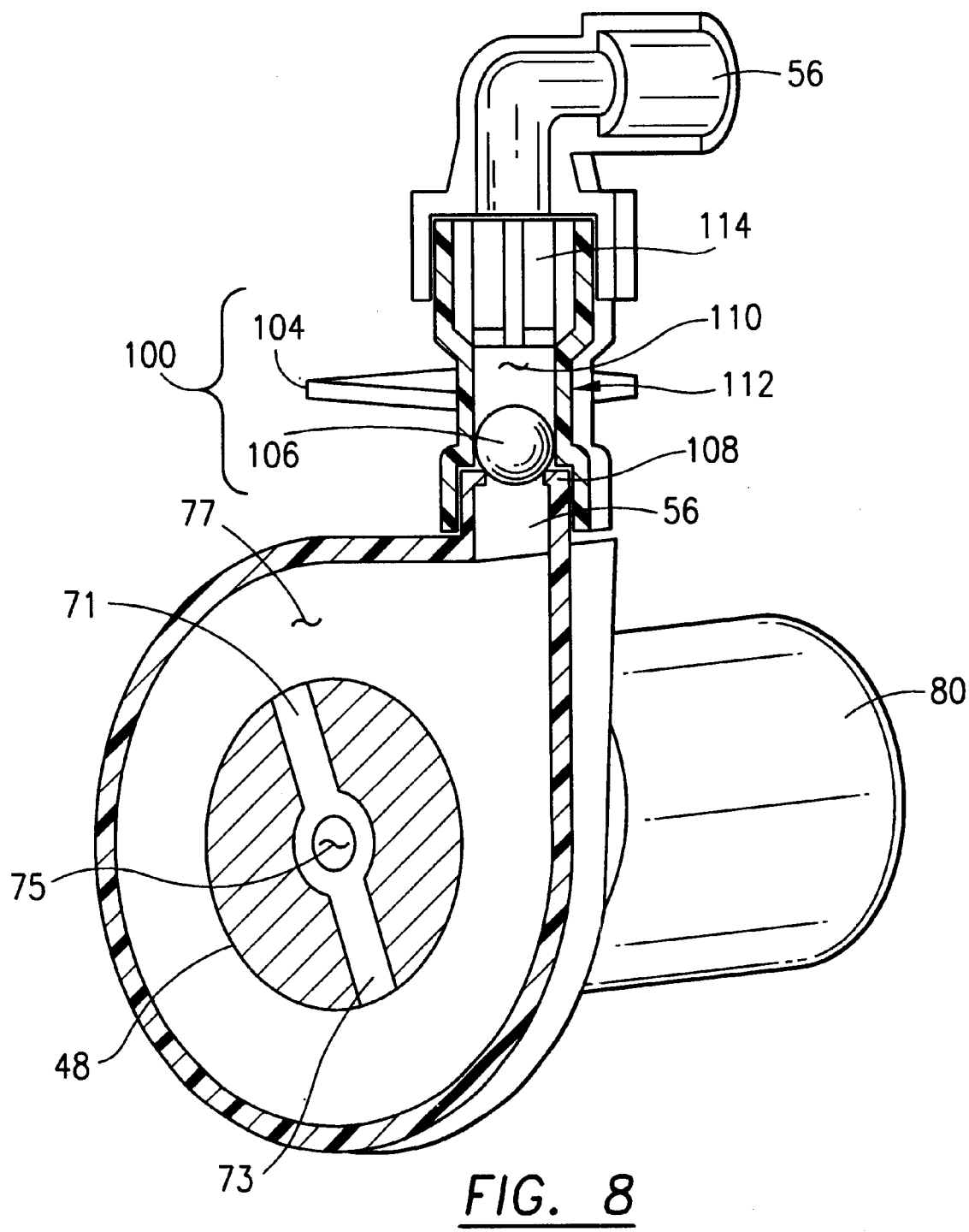
FIG. 8 diagrammatically illustrates the negative buoyancy poppet (preferably a ball), seated at the "leaky" valve seat (which permits fluid flow therethrough less than a system minimal flow), and which illustrates the small flow segment of the flow chamber and the large flow segment of the flow chamber thereabove.

FIG. 8 diagrammatically illustrates a cross sectional view of the automatic pump system 20. System 20 includes a negative buoyancy poppet 106. Although the poppet is illustrated as a ball or sphere, other poppet designs with different shapes may be utilized. For example, poppet 106 may be cylindrical or conical. In FIG. 8, spherical poppet 106 is seated at a "leaky" valve seat 108. Seat 108 is designed such that fluid is permitted to flow therethrough even when poppet 106 is resting or seated thereat. The volume of fluid flowing through seat 108 and therefore through small flow segment 112 and large flow segment 114 when poppet 106 is resting at seat 108 defines a subsystem minimum flow or a sub-minimal flow.

Figure 9A:
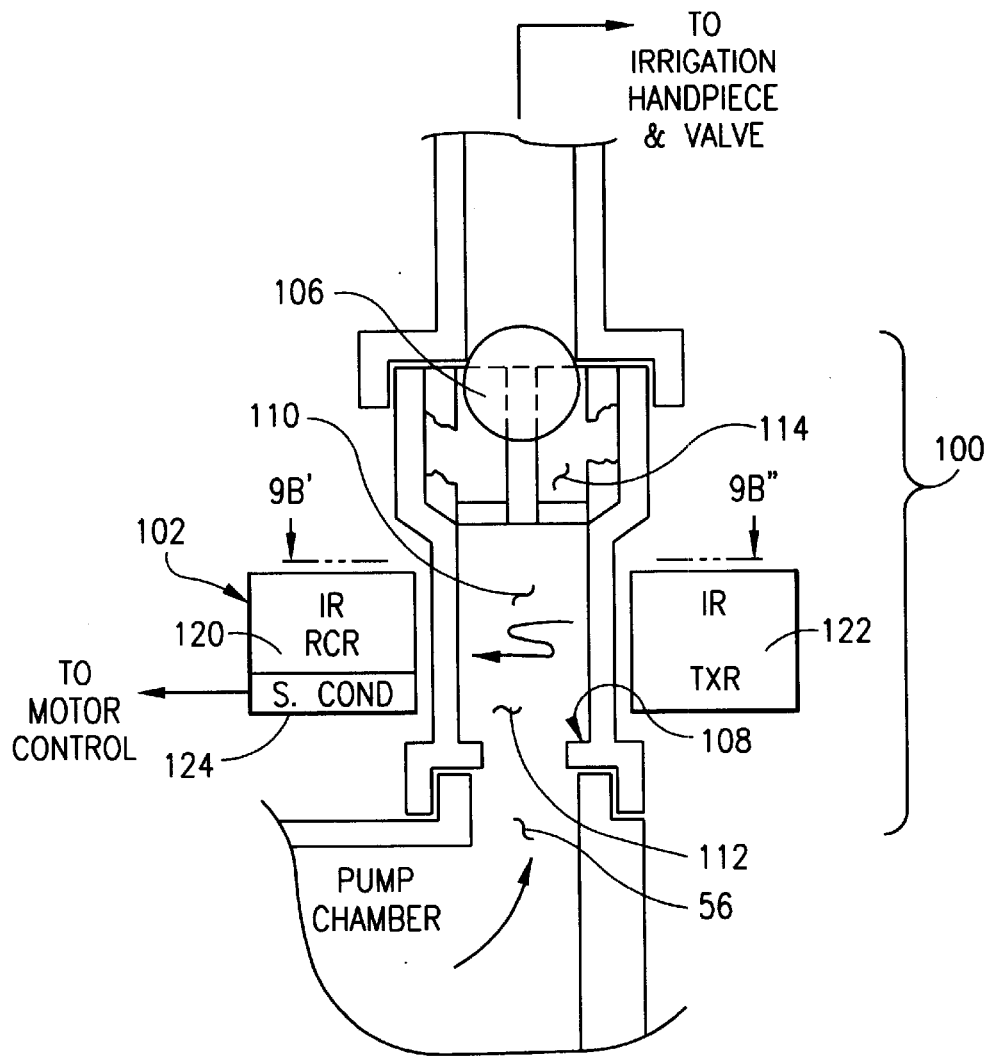
FIG. 9A graphically illustrates a detail of the flow valve chamber including the small flow segment and the large flow segment, and illustrates the poppet (typically a ball) in the large flow segment permitting maximum flow through the flow chamber and illustrates the poppet disposed away from the optical sight line of the optical sensor thereby turning the motor and pump ON, and FIG. 9B is a view of the "leaky" valve seat at the lower en d of the flow chamber from the perspective of section line 9B'–9B"

FIG. 9A is a partial cutaway view of flow sensor 100 of pump system 20. FIG. 9A graphically illustrates a detail of valve flow chamber 110, including small flow segment 112 and large flow segment 114. A ball-shaped poppet 106 is shown in large flow segment 114. As illustrated, the position of poppet 106 allows the maximum volume of fluid to flow through system 20 when the pump is on. Optical sensor 102 includes infrared transmitter 122 and infrared receiver 120 positioned about small flow segment 112 such that the infrared signal generated by transmitter 122 crosses the lower flow segment 112 of flow chamber 110 and is received by receiver 120. The optical characteristics of small flow segment 112 enables transmission of the infrared beam. Receiver 120 is electrically coupled, via appropriate conditioning circuitry, to the motor control circuitry through signal conditioner 124.

Figure 9B:
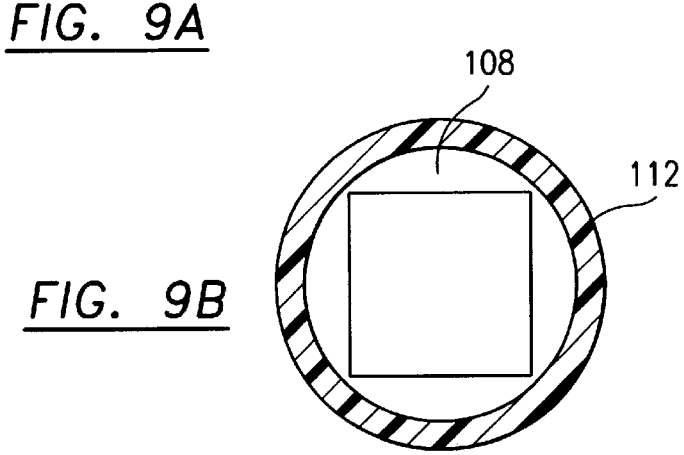

FIG. 9B diagrammatically illustrates a cross-sectional view of "leaky" valve seat 108 in FIG. 9A from the perspective of section line 9B'–9B". Valve seat 108 defines a square opening in flow chamber 110. In the illustrated embodiment, lower small flow segment 112 is defined by a cylindrical tube. Because the poppet in FIG. 9A is spherical, and its diameter is smaller than the diameter of small flow segment 112, when poppet ball 106 is resting at seat 108, fluid is free to flow through the space between the curved surface of poppet 106 and the four corners of seat 108 (see FIGS. 14A and 14B). This sub-minimal flow when the poppet is seated is unique to the present invention.

Figure 11:
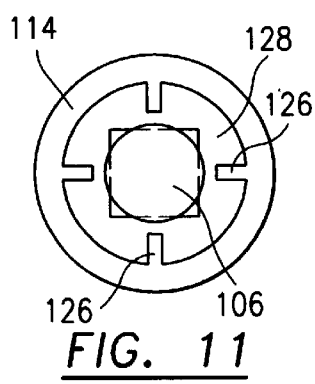
FIGS. 11, 12 and 13 illustrate alternative embodiments of the flow chamber from the perspective of section line 11'–11" in FIG. 10.
Figure 10:
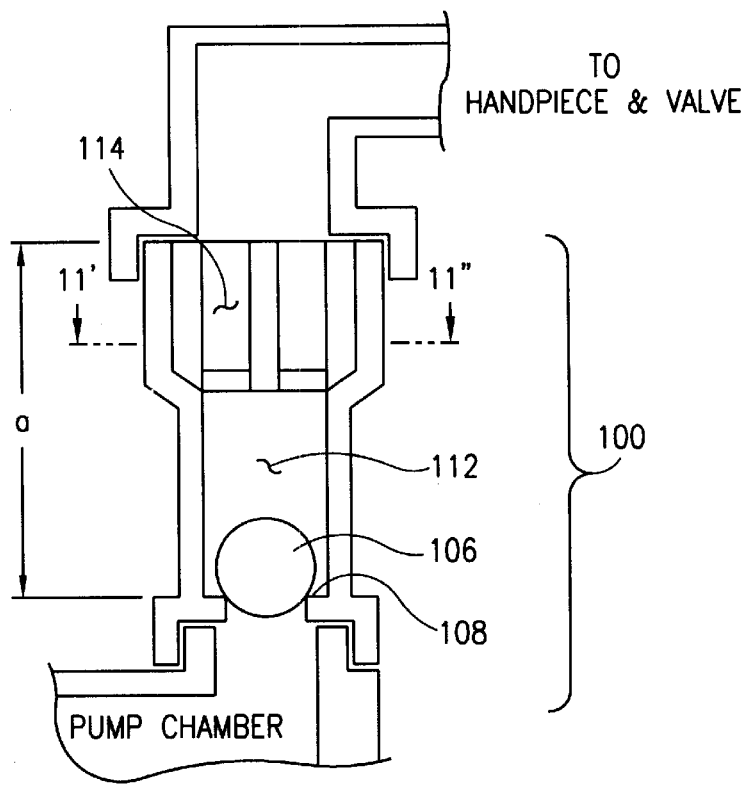
FIG. 10 diagrammatically illustrates the poppet ball in the leaky or sub-system minimal flow valve seat (when the motor and pump is OFF)

FIG. 10 diagrammatically illustrates the poppet valve of flow sensor 100 with poppet 106 resting at seat 108. FIG. 11 diagrammatically illustrates flow sensor 100 from the perspective of section line 11'–11" in FIG. 10. The diameter of the large flow segment 114 is substantially larger than the diameter of poppet 106, thus allowing more fluid to flow through the surrounding spaces 128 when poppet 106 is located within large flow segment 114. Large flow segment 114 also includes radially inboard ribs 126 which guide poppet 106 as it moves to and fro within flow chamber 110. The dashed lines represent the square-shaped opening of seat 108. Because poppet 106 is illustrated in FIG. 10 resting at seat 108, either the remotely located irrigation line control valve (not shown) is off or only slightly open, permitting a sub-minimal fluid flow.

Figure 12:
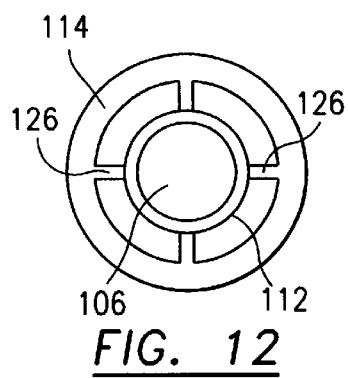
Figure 13:
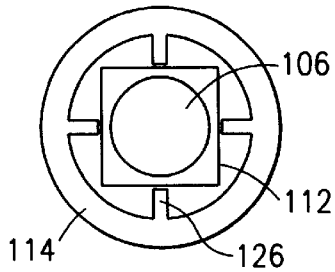

FIGS. 12 and 13 illustrate alternative embodiments of flow sensor 100 viewed from section line 11'–11" in FIG. 10. In FIG. 12, poppet 106 is resting at seat 108 such that the seat opening (not shown) is completely underneath poppet 106. The diameter of the inner wall of lower, small flow segment 112 is larger than the diameter of poppet 106. In FIG. 13, the inner walls of lower, small flow segment 112 define a square. Other shapes can be utilized.

Figure 14A:
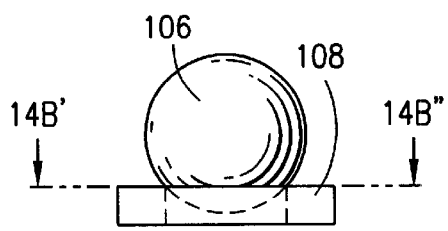
FIGS. 14A and 14B graphically illustrate the ball in the "leaky" seat and the square valve seat (FIG. 14B) which permits sub-system minimal flow therethrough; and, FIGS. 15 and 16 graphically illustrate a position sensor at the pump chamber output and the pump chamber input, respectively.
Figure 14B:
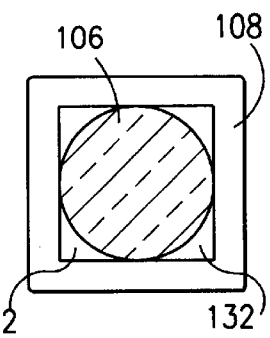

FIGS. 14A and 14B graphically illustrate a spherical poppet 106 resting at "leaky" seat 108. FIG. 14B is a cross-sectional view of poppet 106 and valve seat 108 in FIG. 14A from the perspective of section line 14B'–14B". In FIG. 14B, valve seat 108 is square-shaped which permits sub-system minimal flow through the gaps 132 between poppet 106 and seat 108. Different shapes can be utilized to accomplish the "leaky" valve seat function. For example, seat 108 can define a circular opening with small holes drilled into the seat to permit fluid flow therethrough.

Preferably, flow chamber 110 is perpendicular to the ground plane.

Figure 15:
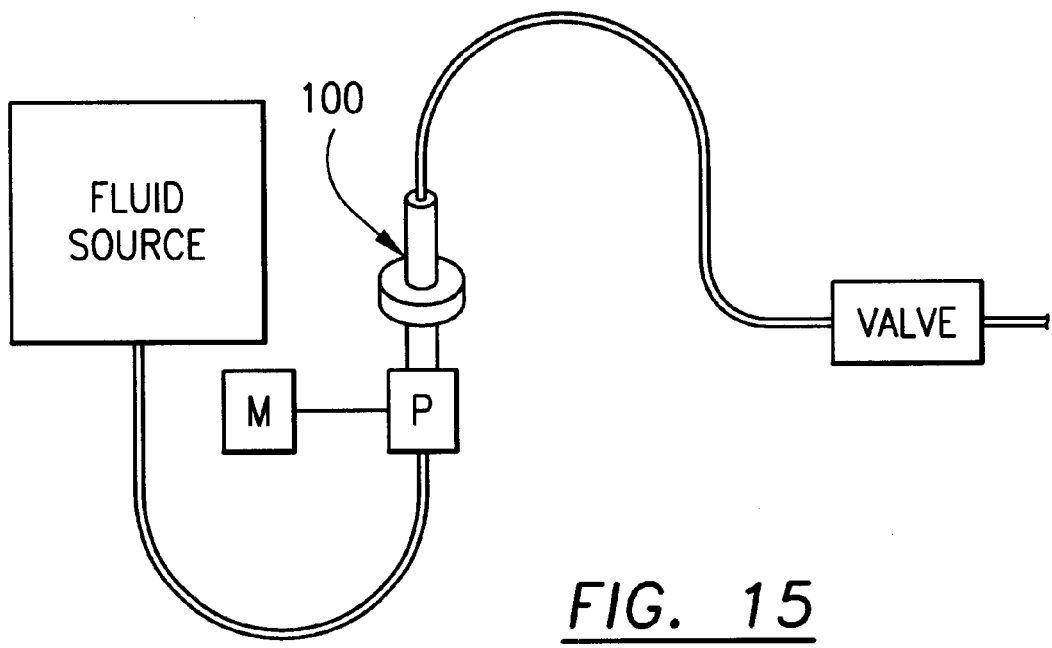
Figure 16:
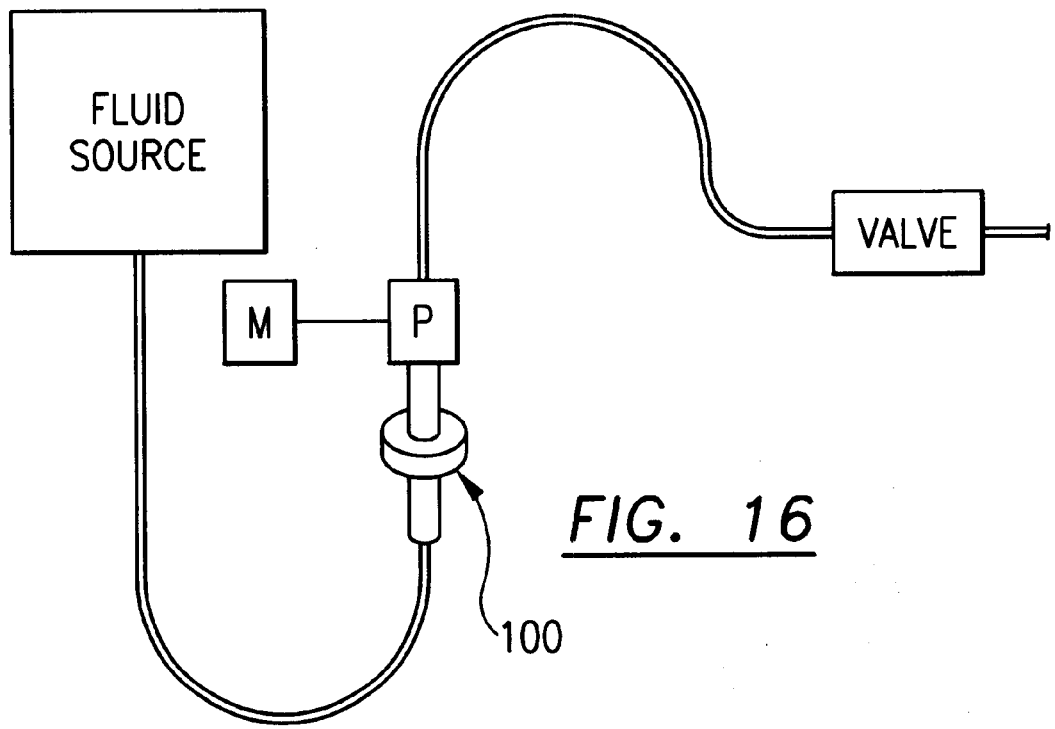

FIGS. 15 and 16 graphically illustrate a position or flow sensor 100 at the pump chamber output and the pump chamber input, respectively.

In operation, automatic pump system 20 supplies pressurized irrigation fluid via output line 25 (see FIG. 1A) to a surgical site 26. Fluid flow is controlled by the health care technician at or near the surgical site by a manual irrigation control valve 32. The manual control valve simply opens and closes supply or output line 25. However, through manipulation of the manual control valve, the health care technician or physician can control the amount of irrigation fluid exiting output line 25 from a few drips at a time to a maximum fluid flow with incremental steps in between such that the present invention provides an "Analog Fluid Flow."

In one embodiment, the "Analog Fluid Flow" provides four conditions: no fluid flow, a sub-minimal fluid flow, a minimal fluid flow, and a maximum fluid flow. When control valve 32 is closed there is fluid flow. When control valve 32 is slightly opened, a sub-minimal flow of irrigation fluid flows from irrigation supply 18, through input line 23, through automatic pump 20, through output line 25 and out to the surgical site 26. During the sub-minimal flow, poppet 106 remains seated on seat 108 within small flow segment 112 of flow chamber 110. The irrigation fluid flows through "leaky" seat 108 permitting a few drops of fluid to exit irrigation line 35. Because poppet 106 remains in small flow segment 112, optical sensor 102 remains disabled (i.e., sensor 102 does not enable motor 80 to turn the pump ON). If the health care technician or physician opens control valve 32 more, poppet 106 lifts off of seat 108 permitting the minimal fluid flow to exit irrigation supply line 35 via output line 25. This minimal fluid flow can range from several drips per second to ready trickle of fluid, depending upon the dimensions of small flow segment 112 and the shape and buoyancy of poppet 106. Different results can be achieved through simple changes to the shape and buoyancy of poppet 106 and the dimensions of flow chamber 110. Finally, if the technician or physician opens manual control valve 32 even more, poppet 106 will move from small flow segment 112 into large flow segment 114 allowing more irrigation fluid to travel through system 20. In addition, motor 80 will turn ON causing the pump to send a maximum fluid flow through the system and out supply line 35.

The optical sensor 102 works as follows. When poppet 106 is in the small flow segment 112, the infrared signal generated by infrared transmitter 122 (see FIG. 9A) is blocked from being received by receiver 120. Thus, circuitry 104 electrically coupling receiver 120 to the motor circuitry via signal conditioner 124, remains in a disabled or OFF state. Once poppet 106 rises above the sight line between transmitter 122 and receiver 120, receiver 120 receives the infrared signal generated by transmitter 122. Receiver 120, through circuit board 104, sends an enabling signal to motor 80, thus turning on the motor and turning the pump ON.

Of course, poppet 106 must be properly constituted to activate the position sensory circuit. Further, the optical position sensor 102 could be moved to the upper large flow segment of the flow chamber (rather than the illustrated lower valve chamber) and the control signal to the motor-pump combination could be inverted. Typical system characteristics are a ¼ inch ball, 270 square inch flow through the large flow segment, about ¼ inch effective flow area in the large flow segment about ¾ inch throw (distance a in FIG. 10).

The claims appended hereto are meant to cover modifications and changes within the scope and spirit of the present invention.

What is claimed is:

1. An automatic pump system for irrigating a surgical site, said pump system adapted to be coupled to a source of surgical fluid via an input line and adapted to deliver a pressurized supply of surgical fluid to a fluid control valving system via an output line, the pump system adapted to be disposed at an elevated position with respect to said fluid control valving system, said pump system comprising:
   a motor and a housing therefor;
   a pump mounted to said housing and mechanically driven by said motor, said pump having a first and a second fluid port respectively adapted to be coupled to said input and output line;
   an electrical system for said motor with at least one battery supplying electrical power to said motor;
   a flow sensor with an optical switch fluidly coupled to one of said first and second fluid ports to determine fluid flow therethrough,
   said flow sensor including a flow chamber with a small flow segment and a large flow segment adjacent thereto, a poppet movably disposed in said flow chamber and sized to permit nominal flow in said small flow segment and large flow in said large flow segment;
   said optical switch configured to accept, as a control input, at least one predetermined poppet position in said flow chamber, said optical switch having a controlled electrical output which is electrically coupled to said electrical system and effective to control application of said electrical power to said pump based upon fluid flow through said flow chamber.

2. An automatic pump system as claimed in claim 1 wherein said poppet has a negative buoyancy in said fluid and said flow chamber is substantially vertically oriented.

3. An automatic pump system as claimed in claim 1 wherein said poppet has a negative buoyancy in said fluid, said flow chamber is substantially vertically oriented and said flow chamber defines, at its lower extremity, a sub-nominal flow poppet seat, said sub-nominal flow poppet seat permitting, when said poppet is disposed thereat, a system minimal flow therethrough.

4. An automatic pump system as claimed in claim 3 wherein said poppet is a ball, and said sub-nominal flow poppet seat is a non-circular seat defining an opening which is irregular with respect to said ball such that said system minimal flow passes therethrough when said ball is on said seat.

5. An automatic pump system as claimed in claim 1 wherein said flow sensor is mounted near or at said second fluid port.

6. An automatic pump system as claimed in claim 1 wherein said controlled electrical output provides an ON-OFF control for said motor and pump via said electrical system.

7. An automatic pump system as claimed in claim 1 wherein said at least one battery is a plurality of batteries which are mounted in a battery sub-housing unit, said battery sub-housing unit mounted on the motor housing.

8. An automatic pump system as claimed in claim 1 wherein said first and second ports define respective hose couplers for said input and output lines, said flow sensor fluidly coupled near or at the second port hose coupler.

9. An automatic pump system for irrigating a surgical site, said pump system adapted to be coupled to a source of surgical fluid via an input line and adapted to deliver a pressurized supply of surgical fluid to a fluid control valving system via an output line, the pump system adapted to be disposed at an elevated position with respect to said fluid control valving system, said pump system comprising:

a motor and a housing therefor;

a pump mounted to said housing and mechanically driven by said motor, said pump having a first and a second fluid port respectively adapted to be coupled to said input and output line;

an electrical system for said motor with at least one battery supplying electrical power to said motor;

a flow sensor having a flow chamber with a small flow segment and a large flow segment fluidly coupled to one of said first and second fluid ports, a poppet movably disposed in said flow chamber and sized to permit nominal flow in said small flow segment and large flow in said large flow segment;

a position sensing switch configured to accept, as a control input, at least one predetermined poppet position in said flow chamber, said position sensing switch having a controlled electrical output which is electrically coupled to said electrical system and effective to control application of said electrical power to said pump based upon fluid flow through said flow chamber.

10. An automatic pump system as claimed in claim 9 wherein said poppet has a negative buoyancy in said fluid and said flow chamber is substantially vertically oriented.

11. An automatic pump system as claimed in claim 9 wherein said poppet has a negative buoyancy in said fluid, said flow chamber is substantially vertically oriented and said flow chamber defines, at its lower extremity, a sub-nominal flow poppet seat, said sub-nominal flow poppet seat permitting, when said poppet is disposed thereat, a system minimal flow therethrough.

12. An automatic pump system as claimed in claim 11 wherein said poppet is a ball, and said sub-nominal flow poppet seat is a non-circular seat defining an opening which is irregular with respect to said ball such that said system minimal flow passes therethrough when said ball is on said seat.

13. An automatic pump system as claimed in claim 12 wherein said flow sensor is mounted near or at said second fluid port.

14. An automatic pump system as claimed in claim 13 wherein said at least one battery is a plurality of batteries which are mounted in a battery sub-housing unit, said battery sub-housing unit mounted on the motor housing.

* * * * *